US008562653B2

(12) United States Patent
Alamin et al.

(10) Patent No.: US 8,562,653 B2
(45) Date of Patent: Oct. 22, 2013

(54) SURGICAL TETHER APPARATUS AND METHODS OF USE

(75) Inventors: Todd Alamin, Woodside, CA (US); Louis Fielding, San Carlos, CA (US); Colin Cahill, Portola Valley, CA (US); Manish Kothari, San Rafael, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 2990 days.

(21) Appl. No.: 12/721,198

(22) Filed: Mar. 10, 2010

(65) Prior Publication Data

US 2010/0234890 A1    Sep. 16, 2010

Related U.S. Application Data

(60) Provisional application No. 61/158,892, filed on Mar. 10, 2009, provisional application No. 61/158,886, filed on Mar. 10, 2009.

(51) Int. Cl.
*A61B 17/88* (2006.01)
*A61B 17/70* (2006.01)

(52) U.S. Cl.
USPC .......................................... 606/279; 606/263

(58) Field of Classification Search
USPC .................... 606/248–249, 257, 263, 279, 74
See application file for complete search history.

(56) References Cited

U.S. PATENT DOCUMENTS

| | | |
|---|---|---|
| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |

(Continued)

FOREIGN PATENT DOCUMENTS

| | | |
|---|---|---|
| EP | 0 322 334 A1 | 6/1989 |
| EP | 0 743 045 A2 | 11/1996 |

(Continued)

OTHER PUBLICATIONS

International Search Report and Written Opinion of PCT Application No. PCT/US2010/026859, mailed May 10, 2010, 12 pages total.

(Continued)

*Primary Examiner* — Eduardo C Robert
*Assistant Examiner* — Julianna N Harvey
(74) *Attorney, Agent, or Firm* — Wilson, Sonsini, Goodrich & Rosati

(57) ABSTRACT

A spinal treatment system includes a constraint device having an upper tether portion, a lower tether portion and a compliance member coupled therebetween. The upper tether portion is coupled with a superior spinous process of a spinal segment in a patient and the lower tether portion is coupled with an inferior spinous process or sacrum of the spinal segment. The length or tension in the constraint device is adjustable so that the construct of the tether portions and the compliance member provides a force resistant to flexion of the spinal segment. The system also includes a first prosthesis coupled with the spinal segment, wherein the constraint device modulates loads borne by the prosthesis or by tissue adjacent thereto.

34 Claims, 11 Drawing Sheets

(56) References Cited

U.S. PATENT DOCUMENTS

| | | | |
|---|---|---|---|
| 4,870,957 A | 10/1989 | Goble et al. |
| 4,955,910 A | 9/1990 | Bolesky |
| 4,966,600 A | 10/1990 | Songer et al. |
| 5,002,574 A | 3/1991 | May et al. |
| 5,011,484 A | 4/1991 | Breard |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,395,374 A | 3/1995 | Miller et al. |
| 5,415,658 A | 5/1995 | Kilpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,609,634 A | 3/1997 | Voydeville |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A | 3/1998 | Bevan et al. |
| 5,797,915 A * | 8/1998 | Pierson et al. ............. 606/74 |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 * | 11/2001 | Asfora ...................... 606/279 |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 | 5/2002 | Castaneda |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,835,207 B2 | 12/2004 | Zacouto et al. |
| 6,899,716 B2 | 5/2005 | Cragg |
| 6,946,000 B2 | 9/2005 | Senegas et al. |
| 7,029,475 B2 | 4/2006 | Panjabi |
| 7,087,083 B2 | 8/2006 | Pasquet et al. |
| 7,101,398 B2 | 9/2006 | Dooris et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,413,576 B2 | 8/2008 | Sybert et al. |
| 7,445,637 B2 | 11/2008 | Taylor |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,559,951 B2 | 7/2009 | DiSilvestro et al. |
| 7,591,837 B2 | 9/2009 | Goldsmith |
| 7,608,094 B2 | 10/2009 | Falahee |
| 7,837,711 B2 | 11/2010 | Bruneau et al. |
| 2002/0173796 A1 * | 11/2002 | Cragg ......................... 606/86 |
| 2003/0088251 A1 | 5/2003 | Braun et al. |
| 2004/0116927 A1 | 6/2004 | Graf |
| 2004/0127989 A1 | 7/2004 | Dooris et al. |
| 2004/0167520 A1 | 8/2004 | Zucherman et al. |
| 2004/0172132 A1 | 9/2004 | Ginn |
| 2004/0243239 A1 * | 12/2004 | Taylor ....................... 623/17.13 |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 * | 6/2005 | Molz et al. ................. 606/61 |
| 2005/0154390 A1 | 7/2005 | Biedermann et al. |
| 2005/0192581 A1 | 9/2005 | Molz et al. |
| 2005/0216017 A1 | 9/2005 | Fielding et al. |
| 2005/0245929 A1 * | 11/2005 | Winslow et al. ........... 606/61 |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 * | 10/2008 | Bennett et al. ............. 606/263 |
| 2008/0281423 A1 | 11/2008 | Sheffer et al. |
| 2008/0312693 A1 | 12/2008 | Trautwein et al. |
| 2008/0319487 A1 | 12/2008 | Fielding et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |
| 2009/0264932 A1 | 10/2009 | Alamin et al. |

(56) References Cited

U.S. PATENT DOCUMENTS

| | | |
|---|---|---|
| 2009/0270918 A1 | 10/2009 | Attia et al. |
| 2010/0004701 A1 | 1/2010 | Malandain et al. |
| 2010/0023060 A1 | 1/2010 | Bennett et al. |
| 2010/0036424 A1 | 2/2010 | Fielding et al. |
| 2010/0234894 A1 | 9/2010 | Alamin et al. |
| 2010/0249839 A1 | 9/2010 | Alamin et al. |

FOREIGN PATENT DOCUMENTS

| | | | |
|---|---|---|---|
| EP | 0743045 | A3 | 12/1996 |
| EP | 1 994 901 | A1 | 11/2008 |
| FR | 2 681 525 | A1 | 3/1993 |
| FR | 2 714 591 | | 7/1995 |
| FR | 2 717 675 | A1 | 9/1995 |
| FR | 2 828 398 | A1 | 2/2003 |
| FR | 2 851 154 | | 8/2004 |
| FR | 2 874 167 | A1 | 2/2006 |
| FR | 2 884 136 | A1 | 10/2006 |
| WO | WO 01/28442 | | 4/2001 |
| WO | WO 02/03882 | A2 | 1/2002 |
| WO | WO 02/03882 | A3 | 5/2002 |
| WO | WO 02/051326 | | 7/2002 |
| WO | WO 02/071960 | | 9/2002 |
| WO | WO 03/045262 | | 6/2003 |
| WO | WO 03/045262 | A3 | 1/2004 |
| WO | WO 2004/052246 | | 6/2004 |
| WO | WO 2004/073532 | | 9/2004 |
| WO | WO 2004/073533 | | 9/2004 |
| WO | WO 2005/110258 | A1 | 11/2005 |
| WO | WO 2008/051423 | | 5/2008 |
| WO | WO 2008/051801 | | 5/2008 |
| WO | WO 2008/051802 | | 5/2008 |
| WO | WO 2008/051806 | | 5/2008 |
| WO | WO 2008/051802 | A3 | 7/2008 |
| WO | WO 2008/051806 | A3 | 7/2008 |
| WO | WO 2008/051801 | A3 | 8/2008 |
| WO | WO 2009/149407 | | 12/2009 |
| WO | WO 2010/028165 | | 3/2010 |
| WO | WO 2010/028165 | A8 | 10/2010 |
| WO | WO 2009/149407 | A9 | 2/2011 |

OTHER PUBLICATIONS

Abbott Spine, Wallis Surgical Technique [Product Brochure], 2006; 24 pages total.

Al Baz et al., "Modified Technique of Tension Band Wiring in Flexion Injuries of the Middle and Lower Cervical Spine," Spine, vol. 20, No. 11, 1995, p. 1241-1244.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

Dickman et al., "Comparative Mechanical Properties of Spinal Cable and Wire Fixation Systems," Spine, vol. 22, No. 6, Mar. 15, 1997, pp. 596-604.

Frymoyer et al., "An Overview of the Incidence and Costs of Low Back Pain" Orthop. Clin. North Am., 1991;22: 263-271.

Garner et al., "Development and Preclinical Testing of a New Tension-Band Device for the Spine: the Loop system," European Spine Journal, vol. 11 (Suppl 2), 2002, pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000, pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000, pp. 489-495.

Medtronic Sofamor Danek USA, Inc., Diam™ System Implant; 2006 [Product Brochure]; downloaded from the Internet: <http://spineinfo.ru/~files/DIAMST.pdf>, 20 pages total.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Biomedical Effects of Flexible Stabilization on the Lumbar Spine," Spine, vol. 22, No. 2, No. 2, Jan. 15, 1997, pp. 151-155.

Sheperd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

* cited by examiner

SURGICAL TETHER APPARATUS AND METHODS OF USE

CROSS-REFERENCES TO RELATED APPLICATIONS

The present application is a non-provisional of, and claims the benefit of U.S. Provisional Patent Application No. 61/158,892 filed Mar. 10, 2009, the entire contents of which are incorporated herein by reference. The present application is also related to U.S. Provisional Patent Application No. 61/158,886. The entire contents of each of the above listed provisional patent applications is incorporated herein by reference.

BACKGROUND OF THE INVENTION

1. Field of the Invention

The present invention generally relates to medical methods and apparatus. More particularly, the present invention relates to methods and apparatus used to restrict flexion of a spinal segment. The methods and apparatus disclosed herein may be used alone or in combination with other orthopedic procedures such as those intended to treat patients with spinal disorders. Exemplary spinal disorders include but are not limited to back pain as well as joint problems, vertebral fractures, intervertebral disc, nucleus and annulus problems.

A host of spinal conditions exist which often result in mobility issues and/or back pain. A major source of chronic low back pain is discogenic pain, also known as internal disc disruption. Discogenic pain can be quite disabling, and for some patients, can dramatically affect their ability to work and otherwise enjoy their lives. Patients suffering from discogenic pain tend to be young, otherwise healthy individuals who present with pain localized to the back. Discogenic pain usually occurs at the discs located at the L4-L5 or L5-S1 junctions of the spine. Pain tends to be exacerbated when patients put their lumbar spines into flexion (i.e. by sitting or bending forward) and relieved when they put their lumbar spines into extension (i.e. by standing or arching backwards). Flexion and extension are known to change the mechanical loading pattern of a lumbar segment. When the segment is in extension, the axial loads borne by the segment are shared by the disc and facet joints (approximately 30% of the load is borne by the facet joints). In flexion, the segmental load is borne almost entirely by the disc. Furthermore, in flexion the nucleus shifts posteriorly, changing the loads on the posterior portion of the annulus (which is innervated), likely causing its fibers to be subject to tension and shear forces. Segmental flexion, then, increases both the loads borne by the disc and causes them to be borne in a more painful way. It would therefore be desirable to provide methods and apparatus that reduce or modulate loading on the disc and adjacent tissue.

A number of treatments exist for addressing back pain and spinal mobility. Some of these include the use of artificial discs, artificial nucleus replacement, annulus repair, kyphoplasty treatment of vertebral fractures, instrumentation of the spinal segment with or without concomitant fusion, and facet joint replacement. Many of these treatments are promising, yet in some cases they also have potential drawbacks. For example, when spinal fusion is performed, excessive motion or loading of spinal segments may result. Often, the excessive motion or loading and consequent effects occur at a level adjacent the fusion (referred to as adjacent segment degeneration or junctional syndrome). This can result in further degeneration of the motion segments. Therefore, it would be desirable if flexion at adjacent level(s) of the spinal segment were restricted, thereby reducing or eliminating the excessive motion and any further degeneration.

Other treatments such as disc replacement, nucleus replacement, annulus repair, facet joint repair, and vertebral fracture repair could also benefit from restricted flexion in the vicinity of treatment area. For example, excessive flexion may loosen the purchase of a prosthesis to the anatomical structures, such as by toggling the pedicle screws that anchor a prosthetic facet joint device. Restricting flexion in the vicinity of the treatment area modulates loads borne by these implants or by surrounding tissue thus reducing, eliminating, or mitigating iatrogenic damage to tissue as well as reducing loads borne by any prostheses and adjacent tissue and further providing additional flexion stability.

For the aforementioned reasons, it would therefore be advantageous to provide methods and apparatus that modulate loads borne by implants used in spinal surgery. It would also be desirable if such methods and apparatus would also modulate loads borne by tissue in the vicinity of the surgically treated region and also provide additional flexion stability. It would further be desirable if the apparatus and methods providing the flexion stability preserved the natural motion and physiology of the patient so as to allow the patient to maintain mobility and minimize or avoid detrimental clinical effects caused by forces resulting from non-physiological loading. It would be further desirable if such methods and apparatus were minimally invasive to the patient, cost effective, and easy to use. It would further be desirable if such methods and apparatus were resistant to damage or failure over repetitive loading conditions in the body.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; 2008/0009866; 2008/0108993; Published PCT Application Nos. WO 01/28442 A1; WO 02/03882 A2; WO 02/051326 A1; WO 02/071960 A1; WO 03/045262 A1; WO2004/052246 A1; WO 2004/073532 A1; WO2008/051806; WO2008/051423; WO2008/051801; WO2008/051802; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3:

319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention generally relates to medical methods and apparatus. More particularly, the present invention relates to methods and apparatus used to restrict flexion of a spinal segment. The methods and apparatus disclosed herein may be used alone or in combination with other orthopedic procedures such as those intended to treat patients with spinal disorders. Exemplary spinal disorders include but are not limited to back pain as well as joint problems, vertebral fractures, intervertebral disc, annulus and nucleus problems.

In a first aspect of the present invention, a surgical method comprises implanting a first prosthesis into the patient where the first prosthesis is engaged with at least a portion of a spinal segment in the patient. The method also includes the step of implanting a constraint device into the patient, with the constraint device having an upper tether portion, a lower tether portion and a compliance member coupled therebetween. An upper portion of the constraint device is engaged with a superior spinous process and a lower portion of the constraint device is engaged with an inferior spinous process or a sacrum. The length or tension in the constraint device is adjusted so that the construct of the tethers and compliance member provides a force resistant to flexion of the spinal segment. The length or tension may be adjusted to a desired value. Also the constraint device modulates loads borne by the first prosthesis or tissue adjacent thereto. The constraint device may indirectly modulate these loads. The first prosthesis may comprise bone graft.

In another aspect of the present invention, a spinal treatment system comprises a constraint device having an upper tether portion, a lower tether portion and a compliance member coupled therebetween. The upper tether portion is coupled with a superior spinous process of a spinal segment in a patient and the lower tether portion is coupled with an inferior spinous process or sacrum of the spinal segment. Length or tension in the constraint device is adjustable so that the construct of the compliance member and tethers provides a force resistant to flexion of the spinal segment. The system also includes a first prosthesis coupled with the spinal segment, wherein the constraint device modulates loads borne by the prosthesis or by tissue adjacent thereto.

In yet another aspect of the present invention, a spinal treatment system comprises a first prosthesis comprising a plurality of pedicle screws and at least one spinal stabilization rod. The first prosthesis is adapted to instrument a pair of vertebrae to be fused. The pair of vertebrae is disposed in a spinal segment of a patient, and at least one pedicle screw is threadably engaged with at least one each of the vertebrae to be fused. The stabilization rod is coupled with the at least one pedicle screw and also the stabilization rod is disposed across the pair of vertebrae to be fused. A constraint device comprises a compliance member, with the constraint device being superior to at least a portion of the pair of vertebrae to be fused. A lower portion of the constraint device is operatively coupled with at least one of the pedicle screws, and the constraint device length or tension is adjustable to so as to provide a force resistant to flexion of the spinal segment superior to the vertebrae to be fused. Alternatively, a lower portion of the constraint device may be operatively coupled directly with one of the fused vertebra, such as by encircling the spinous process of the fused vertebra. The constraint device length or tension may be adjusted to a desired value. The constraint device also modulates loads borne by the first prosthesis and tissue adjacent thereto. The constraint device may comprise an upper tether portion that is disposed at least partially around a superior spinous process or an upper portion of the compliance member may be operatively coupled with a pedicle screw that is threadably engaged with a pedicle superior to the instrumented region of the spinal segment. In alternative embodiments, the embodiment described above may be inverted so that the constraint device may be inferior to at least a portion of the pair of vertebrae to be fused.

Sometimes the first prosthesis may comprise an artificial disc that is implanted between adjacent vertebrae. The disc may be implanted from a posterior, anterior, lateral, or other approach and the adjacent tissue may comprise an intervertebral disc, vertebral body, endplate or facet joints which may be adjacent the artificial disc. In some embodiments, the first prosthesis may comprise an artificial facet joint.

Sometimes, at least one of the first prosthesis or the constraint device may comprise a therapeutic agent that is adapted to modify tissue in the spinal segment. The therapeutic agent may comprise a bone morphogenetic protein or one of its precursors, or another agent whose effect is to modify the load-bearing characteristics of the spinal segment.

The method may further comprise the steps of fusing two adjacent vertebrae together with bone grafting material and implanting the first prosthesis may comprise coupling a substantially inelastic tether to the superior vertebra of the two vertebrae that are fused or will be fused together, wherein the construct of the substantially inelastic tether and lower tether portion limits flexion between the two vertebra that are fused or that will be fused together. The construct of the constraint device also provides a force that is resistant to flexion of the supradjacent or the subjacent motion segment or pair of vertebrae. The substantially inelastic tether also may be disposed between the upper and lower tether portions. The substantially inelastic tether may be disposed at least partially around a superior surface of an intermediate spinous process. The inelastic tether may also be disposed through a notch or hole in intermediate spinous process. Additional disclosure on notching or creating an aperture in a spinous process is disclosed in U.S. Provisional Patent Application No. 61/149,224 filed Feb. 2, 2009, and International PCT Application No. PCT/US2010/022767, the entire contents of which are incorporated herein by reference. The intermediate spinous process may be disposed between the superior spinous process and the inferior spinous process or the sacrum.

Sometimes implanting the first prosthesis comprises positioning a spacer between a pair of adjacent spinous processes. The pair of adjacent spinous processes between which the spacer is implanted may be disposed superior to at least one of the superior spinous process, the inferior spinous process, or the sacrum, and the spacer may inhibit extension of at least a portion of the spinal segment at which it is implanted. The force provided by the construct of the compliance member and tethers may resist flexion of a portion of the spinal segment inferior to the spacer. In other embodiments, implanting the first prosthesis may comprise positioning a spacer between a pair of adjacent spinous processes that are disposed inferior to at least one of the superior spinous process, or the inferior spinous process. The spacer inhibits extension of at least a portion of the spinal segment at which it is implanted and the force provided by the construct of the compliance member and tethers may resist flexion of a spinal segment that is superior to the spacer.

Implanting the first prosthesis may comprise inserting a prosthetic nucleus into a disc disposed between adjacent vertebrae. During segmental flexion, wedging of the vertebral endplates may force the prosthetic nucleus dorsally. Adjusting length or tension in the constraint device may inhibit migration or expulsion of the prosthetic nucleus away from the center of the disc. The tension of the constraint device may be modified or re-adjusted either transcutaneously or in a second surgical procedure. This allows the constraint device to initially be adjusted to a higher tension during an initial period of time after nucleus implantation when greater segmental stiffness is desirable. The higher initial stiffness facilitates soft tissue healing and also minimizes the risk of early nucleus migration from the disc. After the initial healing period, tension may be re-adjusted to a desired value, such as to a lower value in order to decrease segmental stiffness. The method may further comprise fully removing a disc or partially removing disc material between adjacent vertebrae of the spinal segment. The constraint device may modulate loading on the disc space, a prosthetic nucleus placed, or region and any remaining disc material. The constraint device may inhibit re-herniation of the disc after discectomy. The first prosthesis may comprise an annular repair device that is configured to repair or compensate for an injury or defect in an annulus fibrosus of the spinal segment. Implanting the first prosthesis may comprise implanting the annular repair device from a posterior approach. The constraint device may inhibit migration or expulsion of the annular repair device from the annulus fibrosus.

Implanting the first prosthesis may comprise injecting a filler material such as bone cement into a vertebra. Implanting the first prosthesis may comprise treating a fractured vertebra with kyphoplasty or vertebroplasty. The constraint device may modulate loading on the vertebra.

The step of implanting the constraint device may comprise piercing an interspinous ligament to form a penetration superior to superior surface of the superior spinous process and advancing the upper tether portion through the penetration. The step of implanting the constraint device may also comprise piercing an interspinous ligament to form a penetration inferior to an inferior surface of the inferior spinous process and advancing the lower tether portion through the penetration. In other embodiments, the constraint device may be advanced through a notch or aperture in either of the superior or inferior spinous processes, as disclosed in U.S. Provisional Patent Application No. 61/149,224, and International PCT Application No. PCT/US2010/022767 previously incorporated herein by reference. Alternatively, the constraint device may be advanced through a gap between the superior spinous process and an adjacent spinous process, or a gap between the inferior spinous process and an adjacent spinous process. The gap may be created by surgical removal of an interspinous ligament therefrom during a decompression or other procedure. Adjusting length or tension in the constraint device may comprise adjusting the length or tension a plurality of times during treatment of the spinal segment and during or after healing of the spinal segment. Adjusting length or tension may further comprise transcutaneous adjustment after the initial implantation procedure is completed. Sometimes, the region extending directly between an inferior surface of the superior spinous process and a superior surface of the inferior spinous process may remain free of prostheses.

In some embodiments, the method may further comprise fusing a pair of adjacent vertebrae of a spinal segment in a patient. Fusing the pair of adjacent vertebrae may further comprise instrumenting the pair of adjacent vertebrae with a plurality of pedicle screws and at least one stabilization rod disposed therebetween. The method may also comprise implanting a constraint device into the patient, the constraint device engaging a vertebra adjacent to the fused pair of vertebrae, typically immediately superior to but potentially immediately inferior to the fused pair of vertebrae. The constraint device may comprise a compliance member with a portion of the constraint device operatively coupled with a pedicle screw system or coupled directly to one of the fused vertebrae. The method also may include the step of adjusting length or tension in the constraint device, thereby providing a force resistant to flexion of the spinal segment and modulating loads borne by the instrumented adjacent vertebrae and tissue adjacent thereto. The length or tension may be adjusted to a desired a value.

The constraint device may comprise an upper tether portion that is disposed at least partially around or through a superior spinous process. Alternatively, an upper portion of the compliance member may be operatively coupled with a fastener that is coupled with a pedicle superior to the instrumented region of the spinal segment. The fastener may comprise a pedicle screw. In alternative embodiments, the constraint device may also be attached to the inferior adjacent segment. Thus, the constraint device may comprise a lower tether portion that is disposed at least partially around or through an inferior spinous process or sacrum. Alternatively, the lower portion of the compliance member may be operatively coupled with a fastener such as a pedicle screw, that is coupled with a pedicle inferior to the instrumented region of the spinal segment or directly coupled to the spinal segment, inferior of the fused vertebrae.

These and other embodiments are described in further detail in the following description related to the appended drawing figures.

DETAILED DESCRIPTION OF THE INVENTION

Figure 1A:
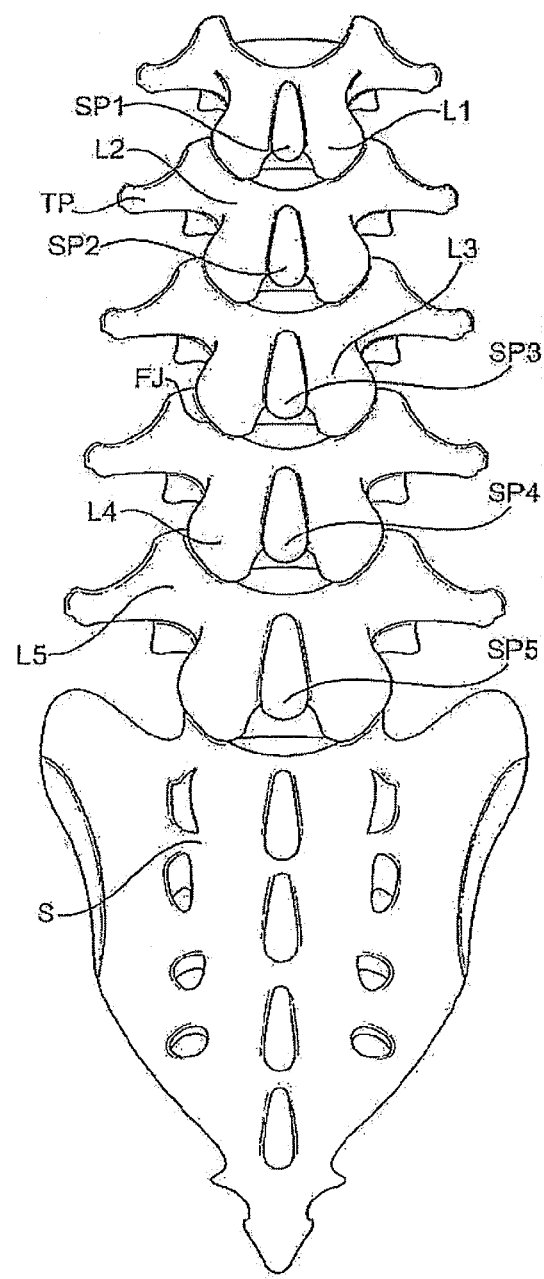
FIG. 1A is a schematic diagram illustrating the lumbar region of the spine.
Figure 1B:
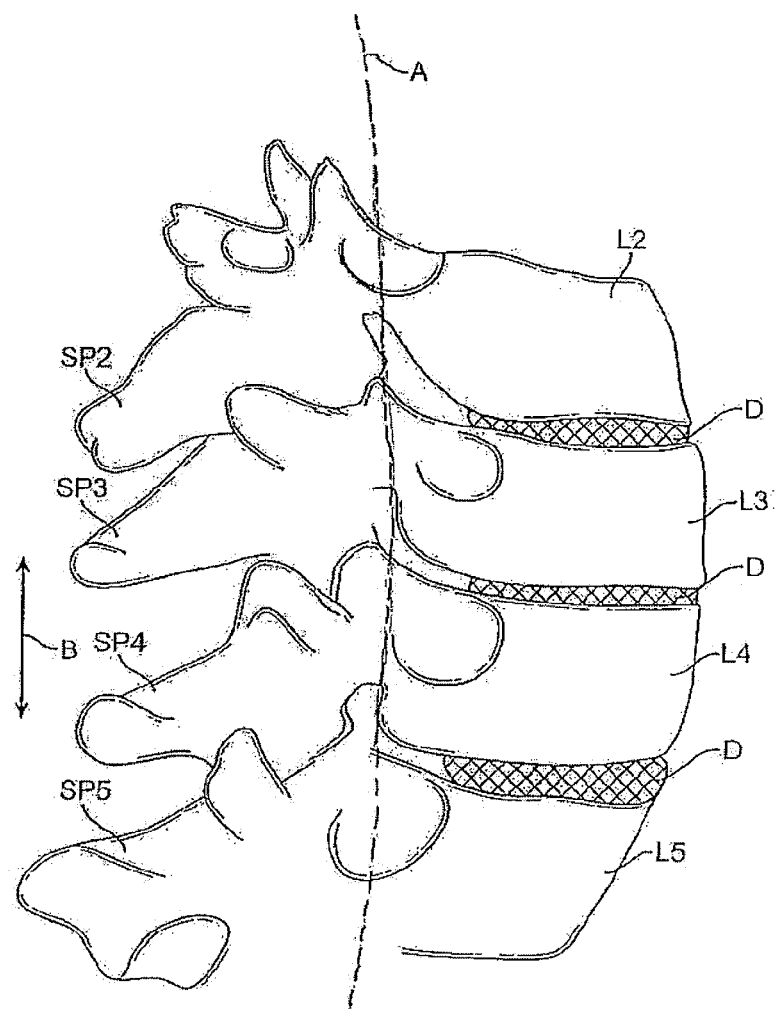
FIG. 1B a schematic illustration showing a portion of the lumbar region of the spine taken along a sagittal plane.

FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the lumbar spine where the spine has a slight anterior convexity and slight posterior concavity. In some cases, the presence of the constraint of the present invention may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae of a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Back pain may be caused by a number of conditions associated with the spinal segment, and many different types of spinal interventions and prostheses have been developed to address such conditions. Examples of treatments administered in an effort to alleviate back pain and related problems include replacement or modification of a disc or disc nucleus, repair of an annulus fibrosus, repair of vertebral fractures with kyphoplasty or vertebroplasty, facet joint replacement, and spinal fusion. These treatments are promising but in some circumstances may have drawbacks. For example, spinal prostheses or surgical procedures may adversely modify loading in the spinal column, causing excessive or otherwise detrimental loads to be borne by the prostheses or by treated or adjacent tissue. Such loads may result in loosening, migration or expulsion of a prosthesis, a significant risk for a prosthetic disc, facet, nucleus, or annular repair device, and a risk also for traditional fusion hardware. In addition, such loads may injure a treated site while it is still healing and vulnerable to mechanical damage and result in iatrogenically damaged tissue; this is particularly true for kyphoplasty. Over time, such loads may lead to degeneration of tissue adjoining a treatment site, as has been observed for segments adjacent to a spinal fusion. Furthermore, such loads may result in increased wear and tear on prostheses, decreasing such prostheses' useful lifetimes and potentially leading to device failures. For example, in the case of artificial discs, the disc edges often impinge on one another thereby causing cracking, wear, tissue inflammation as well as other device failure modes. Often, these detrimental loads are greatest or significantly exacerbated in segmental flexion. Flexion is the largest component of the intervertebral range of motion and is the most frequently exercised; as described previously, flexion increases loading on the intervertebral disc space and is associated with common spinal pathologies. It would therefore be desirable to provide methods and apparatus that can be used alone or in conjunction with other spinal treatments to help reduce the excessive loading and to provide additional flexion stability.

Spinal stabilization is typically accomplished with instrumentation such as pedicle screws and stabilization rods. Placement of such traditional instrumentation in many cases requires major surgery with significant operative morbidities and a long healing period, can be painful, may limit patient mobility, and can result in undesirable wear and tear on the instrumentation itself as well as on adjacent bone and other tissue. Rather than relying on direct stabilization and direct load bearing instrumentation, the present approach disclosed herein utilizes indirect unloading and indirect stabilization of the affected spinal segment by constraining flexion, preferentially biasing the motion of the spinal segment into extension where it is inherently more stable. The spinal segment is biased into this position using an adjustable constraint device that provides a variable force resistant to flexion. Using an indirect approach to augment stability of the spine provides a unique way to improve the mechanical loading environment for implanted spinal devices, surgically treated tissue, and adjacent tissue.

Another major advantage of using the present devices and methods is that no loading other than tensile loading is transferred to the constraint device, and thus the constraint device is likely to experience fewer failure modes than traditional instrumentation in which significant, complex loading is transferred to the screws and rods. The present constraint device therefore, not only attempts to maximize therapeutic effectiveness, but also attempts to minimize failure, while most existing spinal instrumentation maximizes load-bearing and consequentially has a high rate of mechanical failure.

There are other advantages of the present methods and apparatus. For example, traditional instrumentation with pedicle screws and stabilization rods crowds the surgical field and can limit a surgeon's access to a targeted region. In addition, such instrumentation limits the space available for implantation of other devices, especially devices that must be coupled to the spinal segment with screws. The present stabilization methods preferably avoid the use of screws, although screws may be used, allowing implantation of other screw-based devices if necessary. Additionally, less tissue resection is required to implant the present devices and methods relative to traditional instrumentation, providing a less invasive procedure with multiple corresponding clinical and economic benefits including less blood loss, shorter procedure time, faster healing, and a lower treatment cost.

Additionally, when traditional instrumentation such as pedicle screws and rods is used, the spinal segment, once instrumented, is locked into a given position. Even with dynamic stabilization rods, only limited motion is permitted. A rod-and-screw approach thus relies on the skill of the surgeon to determine the optimal position of the spinal segment prior to instrumenting it. The present devices and methods are advantageous because they do not "lock" the spinal segment into a rigid position. The present devices and methods are adjustable in situ and allow some movement of the spinal segment after implantation, reducing the need to establish a single optimal position before the implantation occurs. If this adjustability contributes to more consistent fit between the device and surrounding tissues, healing around the device and in surrounding tissue may occur in a more natural manner. The present devices may also be adjusted in later procedures after initial implantation and are thus likely to be better at accommodating changes over time compared to rigid instrumentation systems.

Another major challenge associated with traditional instrumentation such as rods and screws is the possibility of the devices failing due to shearing, bending, rotation, loosening, etc. The present device is not rigid and can accommodate these types of motions and therefore is less likely to fail in service. Because of its potentially lower failure rate, the present device should generate fewer safety concerns and a lower complication rate.

The present devices and methods also preserve more natural motion of the spinal segment and have unique kinematic signatures compared with other rigid or "flexible" instrumentation devices. Unlike pedicle screw and rod instrumentation, the present devices and methods tend to encourage engagement of the facets. This results in some indirect restriction of axial rotation, which may provide additional spinal segment stability. The present device disclosed herein intentionally allows backward motion (extension) which helps avoid issues with extension loading and may help with balancing of the patient's vertebral column. Most other instrumentation devices or systems do not permit backward motion of the spinal segment.

Figure 2:
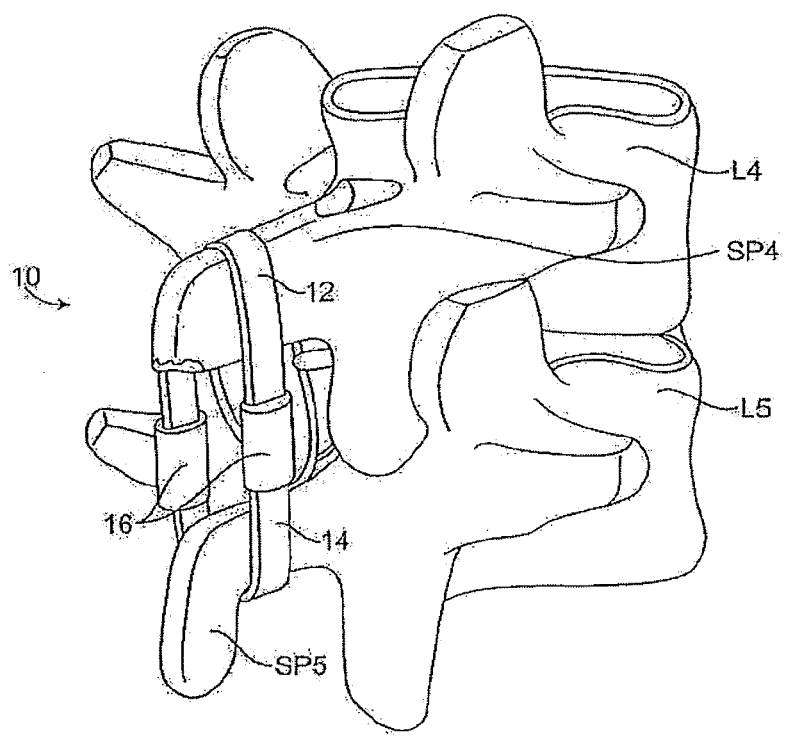
FIG. 2 illustrates a spinal implant of the type described in U.S. Patent Publication No. 2005/0216017A1.

Based on the challenges associated with many existing back pain treatments and stabilization methods, it would therefore be desirable to provide methods and apparatus that can be used alone or in conjunction with other spinal treatments to help reduce the excessive loading and to provide additional flexion stability. FIG. 2 shows a spinal implant of the type described in related U.S. Patent Publication No. 2005/02161017 A1, now U.S. Pat. No. 7,458,981 the entire contents of which are incorporated herein by reference. The constraint device of FIG. 2 may be used alone or in combination with other spinal treatments to modulate loads borne by prostheses implanted into the patient or borne by tissue adjacent the treatment area and to thereby facilitate healing and reduce wear and tear. Furthermore, the constraint device may be used to provide greater stability to the spinal segment.

Many of the prostheses and procedures which can benefit from the constraint described herein were designed to be self-sufficient, such that a specific pathology is directly treated by the intervention. Examples include the treatment of a defect in the annulus fibrosis with an annular repair device and the treatment of a vertebral compression fracture with a kyphoplasty or vertebroplasty. While these interventions directly address the pathology, they often do not address secondary or transitory effects that they precipitate, as described above; as such, a further need for improvement over many stand-alone interventions exists. It should be noted that the adjunctive stabilization may be implanted concurrently with the primary prosthesis or procedure; or may be implanted at a later date to address degenerative changes associated with the detrimental loading of the primary prosthesis or adjacent tissue.

A limited number of implants are known that combine motion-preservation approaches to address multiple pathologies simultaneously; for example, the PDS by Disc Motion Technologies, is a combination of facet replacement device and total disc replacement prosthesis. However, such combination devices are intended to address two independent primary pathologies occurring in combination—for example, the combined disc replacement and facet replacement device addresses combined pathology of the facet joint and the disc. It would be advantageous to provide a means with which improve the results of a primary treatment by augmenting and modulating the biomechanics of the primary treatment. It would further be advantageous for the adjunctive therapy or constraint to be minimally invasive, to avoid the use of pedicle screws due to the known associated complications and morbidities, and to allow for physiologic loading and motion in concert with the intention of the primary motion-preservation treatment.

As illustrated in FIG. 2, an implant 10 typically comprises a tether structure having an upper strap component 12 and a lower strap component 14 joined by a pair of compliance members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which is a force that resists flexion. The force increases as the processes move further apart. Usually, the straps themselves will be essentially non-compliant so that the degree of elasticity or compliance may be controlled and provided solely by the compliance members 16. The implant 10 may be coupled to the spinal segment in a minimally invasive manner. Typically, a small puncture is created in the interspinous ligament (not illustrated) superior to the superior spinous process and also inferior to the inferior spinous process. The upper and lower straps may then be advanced through these piercings and the ends coupled together to form a closed loop. Additional details on implant 10 and the methods of use are disclosed in U.S. Provisional Patent Application Nos. 61/093,922; 61/059,543; 61/059, 538; U.S. patent application Ser. No. 12/106,103; U.S. Patent Publication Nos. 2010/0023060; and 2008/0262549; U.S. Pat. No. 7,458,981; and International PCT Application Nos. PCT/US2009/055914; and PCT/US2009/046492; the entire contents of each is incorporated in its entirety herein by reference. A number of exemplary embodiments in which a constraint device is used in combination with other spinal treatments are disclosed below. The constraint devices disclosed herein may include any of the features described in the references incorporated by reference. Features from various embodiments of constraint devices may also be combined or substituted with features from other embodiments disclosed herein.

Figure 3A:
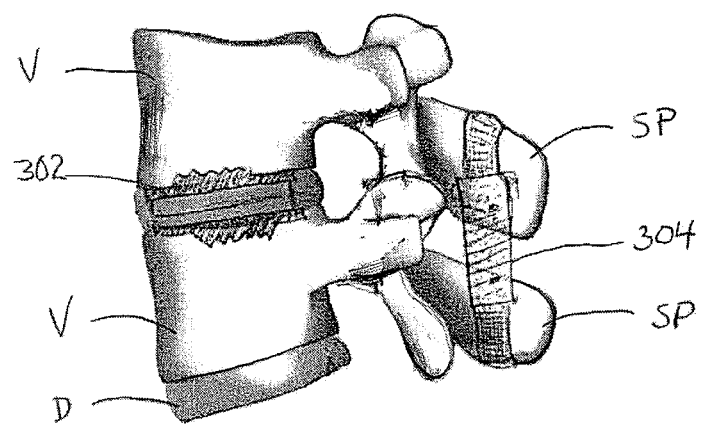
FIGS. 3A-3B illustrate the use of a constraint device with an artificial disc and/or an artificial facet joint.
Figure 3B:
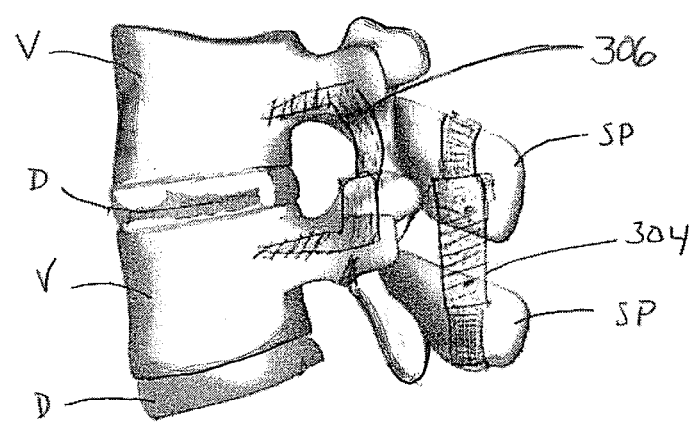

FIGS. 3A-3B illustrate the use of a constraint device with an artificial disc or artificial facet joint replacement device. In FIG. 3A, a natural intervertebral disc D is normally disposed between two adjacent vertebrae V. However, due to disease or degeneration, the damaged disc may be replaced with an artificial disc 302. Artificial discs are well known in the art and exemplary commercial devices include the Charité artificial disc from Depuy Spine, a Johnson & Johnson Company, as well as other devices from Synthes and Medtronic Sofamor Danek. The artificial disc 302 replaces the natural disc D and restores proper alignment and spacing between the two vertebrae V and allows smooth relative motion between the two vertebrae V.

FIG. 3B illustrates the implantation of an artificial replacement facet joint 306 which may be used alone or in combination with the artificial disc implant. Facet joint replacements are also well known in the art such as the Acadia provided by Facet Solutions, Inc. In some patients, facet joints are repaired or replaced with a joint prosthesis in order to eliminate the pathological, painful joint; restore normal motion and provide stabilization of the spinal segment. Also, facet joint implants may be used as an adjunct to partial laminectomy, laminotomy, neural decompression and facetectomy, in lieu of fusion. Facet joint implants are often used to treat instabilities or deformities of the lumbar spine including degenerative disease of the facets, degenerative disease of the facets with instability, degenerative spondylolisthesis and spinal stenosis.

Neither artificial discs nor facet joint replacement devices typically provide an elastic resistance to flexion of the spinal segment. These prostheses have bearing surfaces that are designed to minimize friction and may comprise a "hard stop" that limits travel. Therefore, applying a constraint device 304 around adjacent spinous processes SP helps limit flexion in the spinal segment. Constraint device 304 generally takes the same form as the constraint device illustrated in FIG. 2 and includes an upper tether portion, a lower tether portion and a pair of compliance members (only one illustrated in the lateral view of FIG. 3). The upper tether portion is disposed around a superior surface of a superior spinous process and the lower tether portion is disposed around an inferior surface of an inferior spinous process. The method for applying the constraint device is disclosed in greater detail in U.S. Patent Publication No. 2008/0262549 and additional disclosure on the constraint device may be found in U.S. patent application Ser. No. 12/106,103 and U.S. Pat. No. 7,458,981; all previously incorporated herein by reference. The methods for implanting the constraint device may be applied to any of the embodiments disclosed herein and any of the constraint devices disclosed herein may take the form of constraint device 304. Moreover, by limiting flexion, some of the loading applied to the artificial disc or artificial facet joint and adjacent tissue is modulated. For the disc, this change in loading may minimize disc edge impingement, reducing the need for more complex artificial discs with features that limit edge impingement. The loading is more evenly distributed or even lessened. Thus, applying a constraint device helps restore more natural biomechanics in the spinal segment.

Figure 4A:
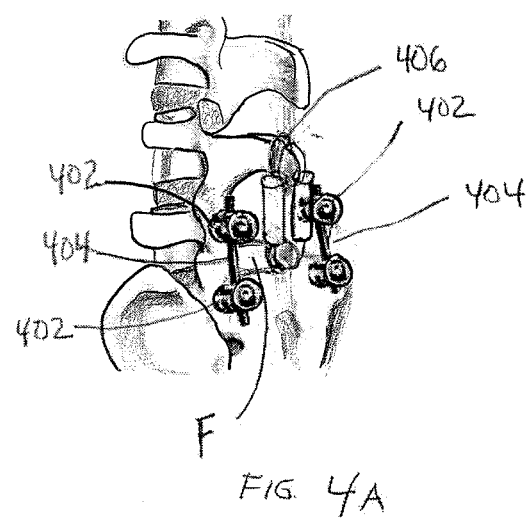
FIGS. 4A-4C illustrate the use of a constraint device supradjacent to a spinal fusion.
Figure 4B:
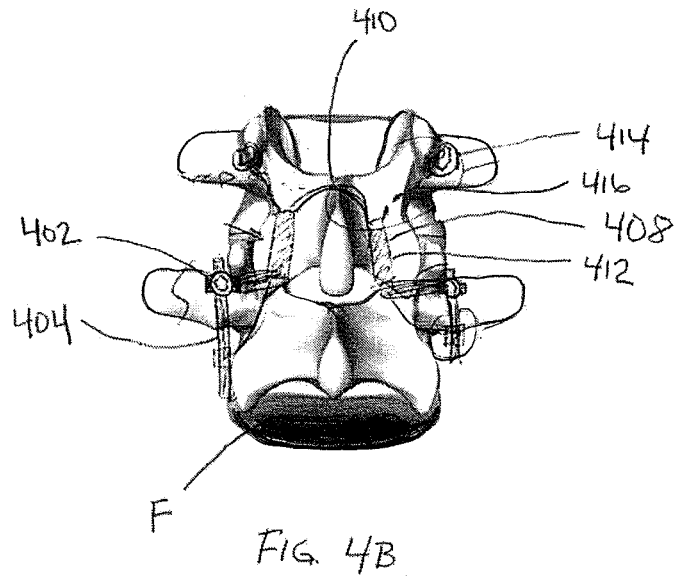
Figure 4C:
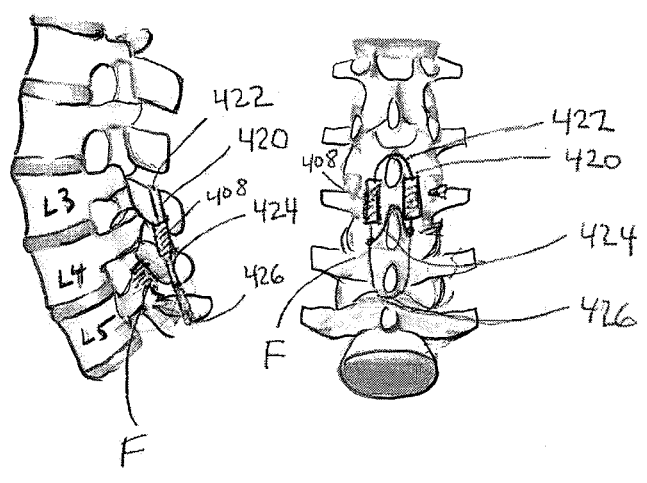

FIGS. 4A-4C illustrate how the constraint device of FIG. 2 may be used in conjunction with fusion of a spinal segment. In FIG. 4A adjacent vertebrae are fused together using methods well known in the art. The fused region F is often instrumented with pedicle screws 402 and spinal stabilization rods 404 to prevent motion at the level of the fusion, although in situ fusions may be performed without internal fixation. While this procedure is promising, it may also have potential drawbacks. For example, after spinal fusion is attained, excessive motion may result at adjacent levels (e.g. spinal segment regions above and below the fused region F). This is due to compensation for loss of flexibility at the fused segment and can result in further degeneration of the motion segments. Therefore, it would be desirable if flexion of segments at adjacent levels (e.g. above or below the fusion) were restricted thereby reducing or eliminating any further degeneration. In FIG. 4A, a constraint device 406 such as the one illustrated in FIG. 2 is applied to the motion segment superior to the fused region. The constraint device is secured to the spinal segment such that it is completely independent of the fusion instrumentation. Here, the constraint device is disposed around the superior surface of a superior spinous process superior to the fusion and also around an inferior surface of an inferior spinous process, the inferior spinous process being a part of superior region of the fused spinal segment. Thus, in this embodiment, motion along the instrumented region is substantially inhibited in order to facilitate the fusion process and the constraint device restricts flexion of the spinal segment supradjacent to the fused region. This helps more evenly distribute and possibly lessen loading applied to the fusion instrumentation as well as adjacent tissue, particularly the adjacent intervertebral disc. It also reduces excessive motion and lessens the chance of further degeneration of the non-fused motion segments.

FIG. 4B illustrates an embodiment similar to that of FIG. 4A with the major difference being that in FIG. 4B, the constraint device is coupled with the fusion instrumentation. In FIG. 4B, the lower vertebra is fused with another vertebra (not illustrated). The fused region F is then instrumented with pedicle screws 402 and spinal stabilization rods 404 to prevent motion between the fused vertebrae. A constraint device 408 is then applied supradjacent to the fused segment. In this embodiment, the constraint device 408 includes an upper tether 410 disposed around a superior surface of a superior spinous process and a pair of compliance members 412 which provide the force resistant to flexion of the spinal segment. Here, the bottom of each compliance member 412 is anchored with the pedicle screw 402 and stabilization rod 404. Thus, the constraint device 408 limits flexion of the spinal segment supradjacent to the fused region F. In alternative embodiments, the upper portion of the compliance member 412 may include a coupling bar 416 illustrated in phantom that is coupled with a pedicle screw or other fastener 414 instead of using the upper tether 410. In alternative embodiments, the constraint could be turned around such that the constraint device is inferior to the fused region and a top portion of the compliance members are coupled with a pedicle screw.

FIG. 4C illustrates lateral and posterior views of an alternative embodiment of a constraint device similar to that of FIG. 2 that may be modified to provide resistance to flexion as well as prevent motion of a fused spinal segment. In FIG. 4C, a posterolateral fusion F is performed between adjacent vertebrae, here L4 and L5. A constraint device 420 includes an upper tether portion 422 and a lower tether portion 426. The constraint device 420 is coupled with the spinal segment such that the upper tether portion 422 is disposed around the superior surface of a superior spinous process of a vertebrae adjacent the fused region and the lower tether portion 426 is disposed around an inferior surface of an inferior spinous process on the inferior portion of the fused region. An intermediate tether 424 is disposed around the superior surface of an intermediate spinous process and the ends of the intermediate tether 424 are secured to the lower tether portion 424. The intermediate spinous process is disposed between the superior and inferior spinous processes to which the constraint device is coupled, and in this exemplary embodiment, the intermediate spinous process is a part of the upper fused vertebra. In this embodiment, the upper, lower and intermediate tether portions 422, 424, 426 are substantially inelastic, thus motion between the inferior spinous process and the intermediate spinous process is controlled based on the tension or length in the tether portions 424, 426. It would therefore be desirable to adjust the intermediate tether portion and the lower tether portion such that no motion or very limited motion is permitted in the fused segment. Additionally, the construct of the upper tether portion 422, the lower tether portion 426 and compliance member 408 restrains flexion of the supradjacent segment. One of skill in the art will appreciate that in alternative embodiments, the constraint device could also be used such that flexion of the spinal segment inferior to the fused region is restricted.

In many of the embodiments disclosed herein, no implant is placed in between the constraint device. Thus, when a constraint device is coupled with a superior surface of a superior spinous process and an inferior surface of an inferior spinous process, the region extending directly between an inferior surface of the superior spinous process and a superior surface of the inferior spinous process often remains free of any spacers or other implants.

Figure 5:
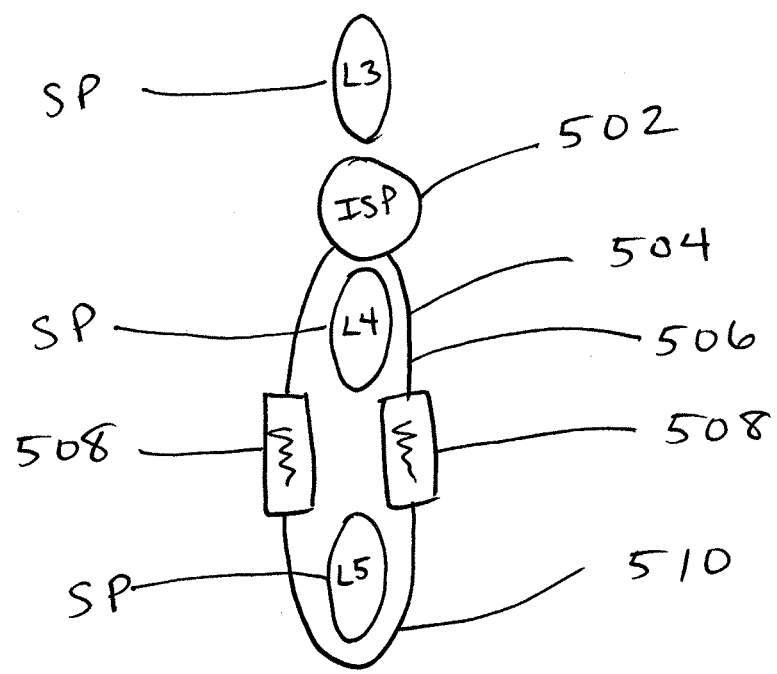
FIG. 5 illustrates the use of a constraint device with an interspinous spacer.

Unlike previous embodiments in which nothing is placed between spinous processes, in FIG. 5 an interspinous spacer is used in combination with a constraint device to limit extension and flexion of spinal segments. In FIG. 5, a spacer 502 such as the X Stop provided by St. Francis Medical Technologies, Inc. (acquired by Kyphon, Inc., now a part of Medtronic) is positioned between spinous processes SP on L3 and L4. The spacer limits extension between adjacent vertebra thereby potentially reducing facet loading and increasing the area of the spinal canal and foramen. This helps relieve patients' systems such as neurogenic claudication and pain. A constraint device 504 may also be applied to the spinal segment in order to limit flexion. In FIG. 5, constraint device 504 includes an upper tether portion 506, compliance members 508 and a lower tether portion 510. The upper tether portion in this embodiment is shown directly coupled with the spacer 502. It may be attached to the spacer with a number of methods including bonding, welding, fixturing, passing it through an aperture, etc. In alternative embodiments the upper tether portion need not be coupled with the spacer. Instead, the tether may be disposed around a superior surface of a superior spinous process similar to the embodiments of FIGS. 2, 3, and 4A-4C previously discussed. The lower tether portion 510 is disposed around an inferior surface of an inferior spinous process. Thus, flexion is limited in the segment inferior to the spacer and the construct of the tethers and compliance members 508 provide a force resistant to flexion. One of skill in the art will appreciate that the spacer may be disposed between any two spinous processes along the spinal segment, thus constraint device position may be moved along the spinal segment as required.

Figure 6A:
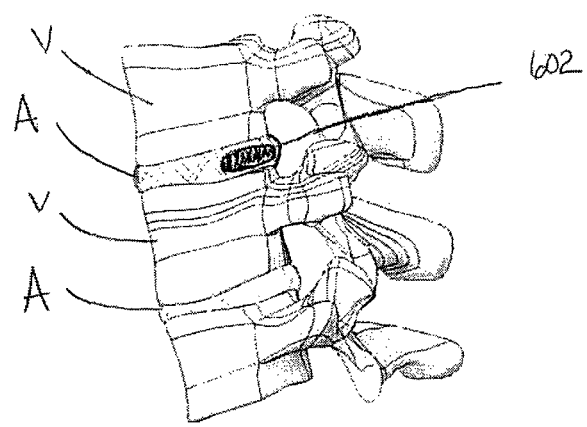
FIGS. 6A-6B illustrate the use of a constraint device with an artificial nucleus.
Figure 6B:
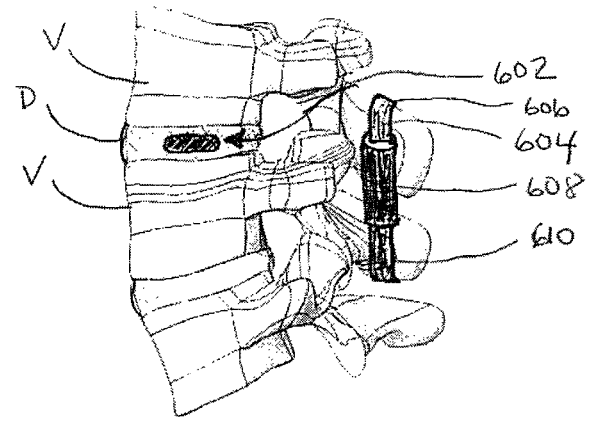

An artificial or prosthetic nucleus may be used instead of a total disc prosthesis when disc degeneration is at an early or intermediate stage and the disc annulus is still competent and provides adequate constraint. By replacing only the nucleus, remaining disc tissues such as the annulus and endplates are preserved along with their functions. The surgical procedure for replacing the nucleus may be simpler than a total disc replacement. In FIG. 6A, an artificial nucleus 602 is implanted into the remaining disc annulus A that is disposed between vertebrae V. The prosthetic nucleus 602 re-inflates the annulus and relieves compressive loads by carrying a portion of the load. However, the nucleus 602 may experience undesired migration, expulsion, wear or other negative effects due to segmental flexion. FIG. 6A illustrates partial extrusion of nucleus 602. A constraint device similar to that of FIG. 2 which restricts flexion may help prevent extrusion of the nucleus. In FIG. 6B, constraint device 604 is applied to the upper and lower spinous processes of the vertebrae surrounding the artificial nucleus 602. The constraint device 604 generally takes the same form as the constraint devices previously described. For example, constraint device 604 includes an upper tether portion 606, a lower tether portion 610 and a pair of compliance members 608 (only one shown in the lateral view of FIG. 6B). The upper tether portion 606 is disposed around a superior surface of a superior spinous process and the lower tether portion 610 is disposed around an inferior surface of an inferior spinous process. Constraint device 604 resists flexion of the spinal segment surrounding the artificial nucleus, thus distributing forces more evenly on the artificial nucleus and surrounding tissue, thereby preventing damage to and expulsion of the nucleus.

Figure 7A:
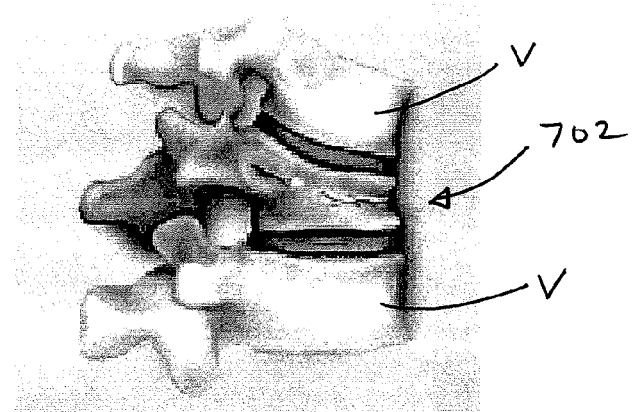
FIGS. 7A-7D illustrate the use of a constraint device in addition to kyphoplasty.
Figure 7B:
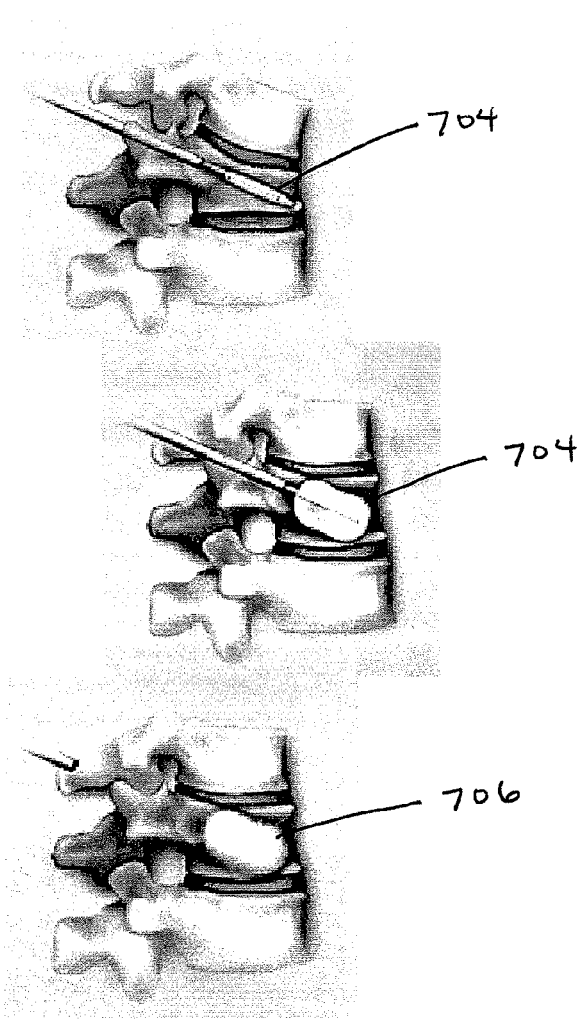
Figure 7C:
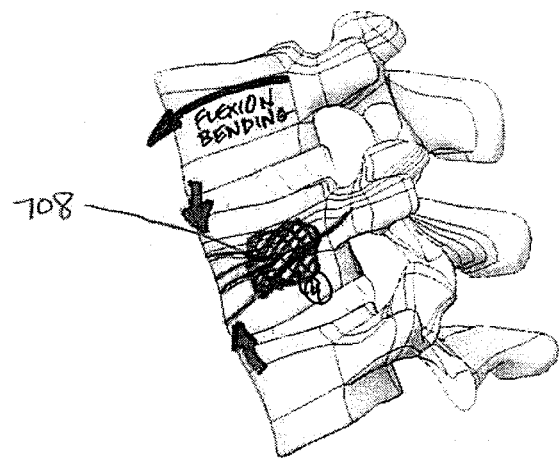
Figure 7D:
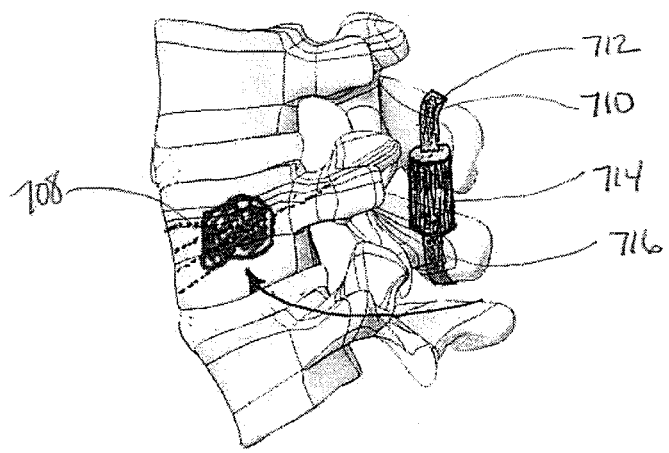

FIGS. 7A-7D illustrate the use of a constraint device in conjunction with kyphoplasty. In patients having a spinal fracture, also referred to as a vertebral compression fracture, often the result of osteoporosis, cancer or benign tumor, kyphoplasty may be an appropriate minimally invasive treatment. FIG. 7A illustrates a spinal fracture 702 in a vertebra V. FIG. 7B illustrates the main steps in a kyphoplasty procedure. In kyphoplasty, a hollow instrument is used to create a narrow pathway into the fractured bone 702. An orthopedic balloon 704 is then inserted through the pathway into the fractured vertebral body 702. Often, two balloons are used, one on each side of the vertebral body, to provide better support to the bone during the treatment (FIG. 7B is a lateral view and therefore only illustrates one balloon). The balloons 704 are then inflated in order to raise the collapsed vertebral body and return it to its normal position. Inflating the balloons also creates a cavity in the bone and once the balloons are deflated, the cavity is filled with bone cement 706 or a bone cement analogue, thereby forming an internal cast that holds the vertebral body in position. Again, this is a promising treatment, but flexion bending motions as indicated by the arrow in FIG. 7C may exert higher compressive loads on the anterior portion of the repaired vertebra. These loads may be transferred to the repaired fracture 708 potentially causing pain, non-union of the fractured bone and other healing failures. In addition, the stiffness of the repaired vertebral body may be greater than that of the native vertebral body because the elastic modulus of bone cement and most bone cement substitutes is greater than that of the normal bone; as such, there could be excessive wear and tear at the bone cement-bone interface. Application of a constraint device that limits flexion may help offload the repaired fracture and adjacent tissues 708 thereby reducing these adverse complications. In FIG. 7D a constraint device similar to that of FIG. 2 is applied to the spinal segment treated with kyphoplasty. The constraint device 710 generally takes the same form as previously described above. The constraint device 710 includes an upper and lower tether portion 712, 716 that are disposed around the spinous processes adjacent the spinal fracture. In this embodiment, the upper tether portion 712 is disposed around a superior surface of a superior spinous process and the lower tether portion 716 is disposed around an inferior portion of an inferior spinous process of the fractured vertebra. The construct of the tethers and a pair of compliance members 714 (only one illustrated in the lateral view of FIG. 7D) provide the force resistant to flexion of the treated spinal segment. Other embodiments may include variations on kyphoplasty including but not limited to vertebroplasty (injection of a filler material without expansion of the kyphoplasty balloon) and implants (e.g. implantation of stent-like or mesh-like devices).

Figure 8A:
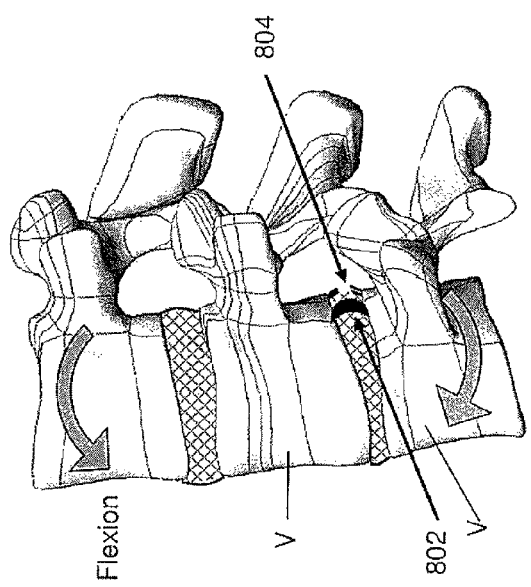
FIGS. 8A-8B illustrate the use of a constraint device with an annular repair device.
Figure 8B:
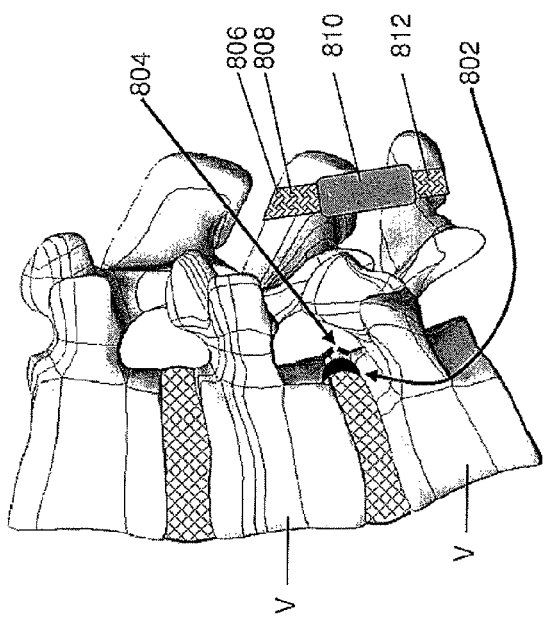

FIGS. 8A-8B illustrate the use of a constraint device with an annular repair device. Annular repair devices are used to patch or repair a defect, lesion, tear or other injury in the annulus fibrosus, especially one due to a disc herniation. FIG. 8A illustrates an annular defect 804 in an intervertebral disc between adjacent vertebrae V. An annular repair device 802 is coupled with the annulus in order to prevent disc herniation or nucleus expulsion. Herniations are often acutely associated with flexion, indicated in FIG. 8A by the arrows, which may also inhibit healing and induce re-herniation. Similarly, flexion motions may place more demands on annular repair devices, thus impacting their effectiveness. A constraint device that restricts flexion motions may help reduce the incidence of re-herniation and improve outcomes for patients treated with an annular repair device, in particular a minimally invasive device.

FIG. 8B illustrates the use of a constraint device such as the one seen in FIG. 2 in conjunction with the annular repair device 802. The constraint device generally takes the same form as those previously described above. Constraint device 806 includes upper and lower tether portions 808, 812 and a pair of compliance members 810 (only one seen in the lateral view of FIG. 8B). The upper tether portion is disposed around a superior surface of a superior spinous process and the lower tether portion is disposed around an inferior surface of an inferior spinous process. The construct of the tethers and compliance members 810 provide a force that limits flexion of the spinal segment. This also helps to reduce tension in the posterior annulus and keeps the annular defect 804 closed.

In any of the embodiments disclosed above, tension and or length of the constraint device may be adjusted in order to control how much resistance to flexion is provided. The constraint devices may be adjusted before, during or after implantation including transcutaneously so that additional surgery is avoided. This also allows the device to be adjusted as healing occurs. For example, a tighter constraint device that provides greater resistance to flexion may be provided during the initial phase of healing and a less tight constraint device that provides less resistance to flexion may be required as healing progresses. Various adjustment and locking mechanisms are disclosed in U.S. Provisional Patent Application Nos. 61/059,543; and 61/059,538; previously incorporated herein by reference, as well as other patent applications incorporated herein. Furthermore, any of the embodiments disclosed herein may also be used to carry and deliver a therapeutic agent that facilitates the healing process. For example, antibiotics may be carried by the constraint device to help prevent infection and bone morphogenetic proteins may also used in order to help stimulate bone or other tissue growth. Additionally, many of the embodiments disclosed herein show the constraint device limiting flexion of a spinal segment at the level of or superior to the level of the implant or treatment. One of skill in the art will appreciate that the constraint device may be applied to the spinal segment so as to limit flexion below the level of the implant or treatment. In addition, in some situations a lower portion of the constraint device may be coupled with the sacrum instead of an inferior spinous process. Sacral attachment methods are disclosed in greater detail in U.S. Provisional Patent Application No. 61/149,224; International PCT Application No. PCT/US2010/022767; and U.S. patent application Ser. No. 11/827,980, the entire contents of which are incorporated herein by reference. In the embodiments described above, the constraint structure may be implanted concurrently with the first prosthesis or procedure, or in a separate procedure performed at another time.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the independent claims.

What is claimed is:

1. A surgical method comprising:
  implanting a first prosthesis into a patient, the first prosthesis comprising fusion instrumentation coupled to at least a portion of a spinal segment comprising a first and a second vertebra;
  implanting a constraint device into the patient, the constraint device having at least one tether portion, and at least one compliance member coupled to the at least one tether portion,
  wherein at least one portion of the constraint device is engaged with a spinous process of a third vertebra superior to or inferior to the instrumented portion of the spinal segment,
  and at least one portion of the constraint device is attached to at least one portion of the fusion instrumentation, and
  wherein the compliance member comprises an elastic member; and
  adjusting length or tension in the constraint device so that a construct of the at least one tether portion and the at least one compliance member provides an elastic force resistant to flexion of the spinal segment, and
  wherein the constraint device modulates loads borne by the first prosthesis or tissue adjacent thereto.

2. The method of claim 1, wherein the constraint device indirectly modulates loads borne by the first prosthesis or tissue adjacent thereto.

3. The method of claim 1, wherein the adjacent tissue comprises an intervertebral disc.

4. The method of claim 1, wherein the first prosthesis further comprises a bone graft.

5. The method of claim 1, wherein the first prosthesis further comprises a pedicle screw.

6. The method of claim 1, wherein the first prosthesis further comprises a stabilization rod disposed between adjacent vertebrae.

7. The method of claim 1, wherein at least one of the first prosthesis or the constraint device comprises a therapeutic agent adapted to modify tissue in the spinal segment.

8. The method of claim 7, wherein the therapeutic agent comprises a bone morphogenetic protein.

9. The method of claim 1, further comprising re-adjusting length or tension in the constraint device in a second separate procedure.

10. The method of claim 1, wherein adjusting length or tension is performed transcutaneously.

11. The method of claim 1, further comprising full or partial discectomy of disc material between adjacent vertebrae of the spinal segment.

12. The method of claim 11, wherein the constraint device inhibits re-herniation of the disc after discectomy.

13. The method of claim 1, wherein the constraint device modulates loading on the disc space.

14. The method of claim 1, wherein the constraint device modulates loading on the vertebra.

15. The method of claim 1, wherein the step of implanting the constraint device comprises:
  piercing an interspinous ligament to form a penetration superior to a superior surface of a spinous process of at least one vertebra; and
  advancing a first tether portion through the penetration.

16. The method of claim 1, wherein the step of implanting the constraint device comprises:
  piercing an interspinous ligament to form a penetration inferior to an inferior surface of a spinous process of at least one vertebra; and
  advancing a first tether portion through the penetration.

17. The method of claim 1, wherein the step of implanting the constraint device comprises:
  advancing a tether portion through a gap between a spinous process and an adjacent spinous process, the gap created by surgical removal of an interspinous ligament therefrom.

18. The method of claim 1, wherein the step of implanting the constraint device comprises: advancing the at least one tether portion through a gap between the inferior spinous process of the spinal segment and an adjacent spinous process, the gap created by surgical removal of an interspinous ligament therefrom.

19. The method of claim 1, wherein adjusting length or tension in the constraint device comprises adjusting the length or tension a plurality of times during treatment of the spinal segment and during or after healing of the spinal segment.

20. The method of claim 19, wherein the length or the tension is adjusted transcutaneously.

21. The method of claim 1, wherein adjusting length or tension in the constraint device comprises adjusting the length or the tension to a desired value.

22. The method of claim 1, wherein a region extending directly between a spinous process of the first vertebra in the spinal segment and a spinous process of the second vertebra in the spinal segment remains free of prostheses.

23. The method of claim 1, further comprising allowing extension of at least the spinous process of the third vertebra.

24. The method of claim 1, further comprising: fusing two adjacent vertebrae together, and wherein implanting the first prosthesis further comprises coupling a substantially inelastic tether to a superior vertebra of the two vertebra to be fused, wherein a construct of the substantially inelastic tether and an additional lower tether limits flexion between the two fused vertebra, and wherein the substantially inelastic tether is disposed between an additional upper and an additional lower tether portions.

25. The method of claim 24, wherein the substantially inelastic tether is disposed at least partially around a superior surface of an intermediate spinous process, the intermediate spinous process disposed between a superior spinous process and an inferior spinous process or as sacrum.

26. The method of claim 1, wherein implanting the first prosthesis further comprises positioning a spacer between a pair of adjacent spinous processes, the pair of adjacent spinous processes disposed superior to at least one of a superior spinous process, an inferior spinous process, or a sacrum, the spacer inhibiting extension of at least a portion of the spinal segment, and wherein the force resists flexion of a portion of the spinal segment inferior to the spacer.

27. The method of claim 1, wherein implanting the first prosthesis further comprises positioning a spacer between a pair of adjacent spinous processes, the pair of adjacent spinous processes disposed inferior to at least one of a superior spinous process or an inferior spinous process, the spacer inhibiting extension of at least a portion of the spinal segment, and wherein the force resists flexion of a portion of the spinal segment superior to the spacer.

28. A surgical method comprising:
fusing a pair of adjacent vertebrae of a spinal segment in a patient together, the pair of adjacent vertebra comprising a first and a second vertebra;
instrumenting the pair of adjacent vertebrae;
implanting a constraint device into the patient, the constraint device superior to or inferior to at least a portion of the instrumented pair of vertebrae, the constraint device comprising a compliance member, wherein a portion of the constraint device is attached to the instrumentation of the adjacent fused vertebrae, and wherein the compliance member comprises an elastic member; and
wherein the constraint device is engaged with a spinous process of a third vertebra superior to or inferior to the pair of fused vertebrae; and
adjusting length or tension in the constraint device thereby providing an elastic force resistant to flexion of the spinal segment and modulating loads borne by the instrumented adjacent vertebrae and tissue adjacent thereto.

29. The method of claim 28, wherein the constraint device comprises an upper tether portion disposed at least partially around the spinous process of the first vertebra or the second vertebra.

30. The method of claim 28, wherein a portion of the compliance member is operatively coupled with a fastener, the fastener coupled with a pedicle of the first vertebra or the second vertebra.

31. The method of claim 30, wherein the fastener comprises a pedicle screw.

32. The method of claim 28, wherein the pair of adjacent vertebrae are instrumented with a plurality of pedicle screws and at least one stabilization rod disposed therebetween.

33. The method of claim 28, wherein the constraint device comprises an inferior tether portion disposed at least partially around the spinous process of the third vertebra.

34. The method of claim 24, further comprising allowing extension of at least the third vertebra.

* * * * *